US006414125B1

(12) United States Patent
Siekmann et al.

(10) Patent No.: US 6,414,125 B1
(45) Date of Patent: Jul. 2, 2002

(54) METHOD OF CHROMATOGRAPHICALLY PURIFYING OR FRACTIONATING, RESPECTIVELY, VON WILLEBRAND FACTOR FROM A VWF-CONTAINING STARTING MATERIAL

(75) Inventors: Juergen Siekmann, Vienna; Peter Turecek, Klosterneuburg; Hans-Peter Schwarz, Vienna; Johann Eibl, Vienna; Bernhard Fischer, Vienna; Artur Mitterer, Mannsdorf; Friedrich Dorner, Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/355,865

(22) PCT Filed: Jan. 30, 1998

(86) PCT No.: PCT/AT98/00020

§ 371 (c)(1),
(2), (4) Date: Oct. 21, 1999

(87) PCT Pub. No.: WO98/33820

PCT Pub. Date: Aug. 6, 1998

(30) Foreign Application Priority Data

Feb. 4, 1997 (AT) .............................................. 176/97

(51) Int. Cl.$^7$ ................................................. A23J 1/00
(52) U.S. Cl. ...................... 530/413; 530/412; 530/350; 530/300; 530/330; 260/12
(58) Field of Search .......................... 260/112; 530/330, 530/350, 300, 413, 412

(56) References Cited

U.S. PATENT DOCUMENTS

| 4,331,766 A | 5/1982 | Becker et al. ............... 435/273 |
| 4,640,834 A | 2/1987 | Eibl et al. ...................... 424/94 |
| 4,814,277 A | 3/1989 | Eibl et al. ................... 435/269 |
| 4,814,435 A | 3/1989 | Schwarz et al. ............ 530/383 |
| 5,408,039 A | 4/1995 | Burnouf-Radosevich et al. 530/383 |
| 5,410,022 A | 4/1995 | Eibl et al. ................... 530/383 |
| 5,610,147 A | 3/1997 | Seelich ......................... 514/21 |
| 5,639,730 A | 6/1997 | Eibl et al. ..................... 514/21 |
| 5,733,885 A | 3/1998 | Eibl et al. ..................... 514/21 |

FOREIGN PATENT DOCUMENTS

| AT | 391 808 B | 11/1986 |
| CA | 2063872 | 11/1995 |
| EP | 0 023 607 A2 | 2/1981 |
| EP | 0 131 740 A3 | 6/1984 |
| EP | 0 159 311 A1 | 2/1985 |
| EP | 0 247 998 A2 | 5/1987 |
| EP | 0 506 651 A2 | 3/1992 |
| EP | 0 503 991 A1 | 9/1992 |
| EP | 0 567 448 A1 | 4/1993 |
| EP | 0 637 451 A1 | 8/1994 |
| WO | 600480 * | 2/1993 |
| WO | WO 94/13329 | 6/1994 |

OTHER PUBLICATIONS

Santoro et al., Collagen, Rel. Res., vol.2, pp. 31–43, 1982.*
Brown et al., Thrombosis Research, vol. 43, pp. 303–311, 1986.*
Santoro, S.A. and Cowan, J.F., "Adsorption of von Willebrand Factor by Fibrillar Collagen–Implications Concerning the Adhesion of Platelets to Collagen", *Collagen Rel. Res.*, vol. 2, 1982, pp. 31–43, XP002068370.
Brown, J.E. et al., "An Elisa Test for the Binding of von Willebrand Factor Antigen to Collagen" *Thromb. Res.*, vol. 43, 1986, pp. 303–311, XP002068371.
International Search Report for PCT/AT98/00020, dated Jun., 30, 1998.
Pool, J.G., and Shannon, A.E., "Production of High–Potency Concentrates of Anthihemophilic Globulin in a Closed–bag System", *New Eng. J. of Med.*, vol. 273, 1965, pp. 1443–1447.
Bradford, M.M., "A Rapid and Sensitive Method for the Quantitation of Microgram Quantities of Protein Utilizing the Principle of Protein–Dye Binding" *Rep. Res.* Lab., 1976, pp. 248–254.
Santoro S.A., "Adsorption of von Willebrand Factor/Factor VIII by the Genetically Distinct Intersitial Collagens" *Thromb. Res.*, vol. 21, 1981, pp. 689–693.
Santoro, S.A., "Preferential Binding of High Molecular Weight Forms of von Willebrand Factor to Fibrillar Collagen" *Biochimeca et Biophysica Acta.*, vol. 756, 1983, pp. 123–126.
Kessler, C.M., et al., "Collagen–Factor VIII/von Willebrand Factor Protein Interaction", *Blood*, vol. 63, 1984, pp. 1291–1298.
Hörmann H., "Zur Biochemie und Physiologie der Kollagentypen", *Hämostaseologie*, vol. 10, 1990, pp. 138–146.
Fischer, B.E., et al., "Effect of Multimerization of Human and Recombinant von Willebrand Factor on Platelet Aggregation, Binding to Collagen and Binding of Coagulation Factor VIII", *Throm. Res.*, vol. 84, 1996, pp. 55–66.

* cited by examiner

Primary Examiner—Karen Cochrane Carlson
Assistant Examiner—Hope A. Robinson
(74) Attorney, Agent, or Firm—Townsend and Townsend and Crew LLP

(57) ABSTRACT

Disclosed is a method of chromatographically purifying or fractionating, respectively, von Willebrand factor (vWF) from a vWF-containing starting material, comprising the following steps:
- adsorbing the vWF from the starting material on avid collagen immobilized on a carrier,
- separating the non-adsorbed portion and, optionally, washing the carrier,
- eluting the vWF from immobilized collagen, and
- recovering the purified vWF, as well as a pharmaceutical preparation comprising biologically active vWF which is bound to collagen in a stable manner.

47 Claims, 1 Drawing Sheet

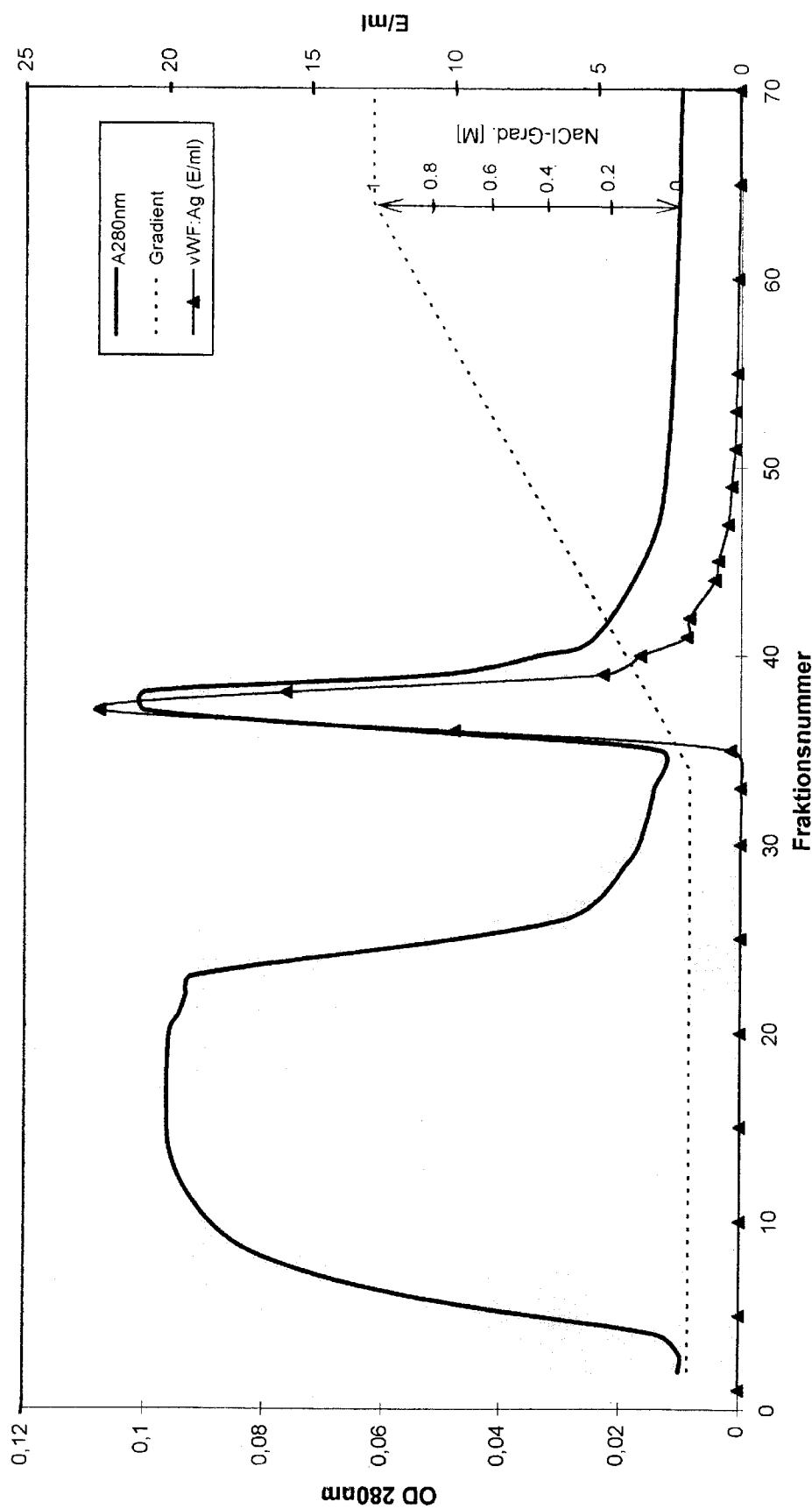
FIG. 1 Affinitätschromatographische Reinigung von vWF über Collagen-Agarose

METHOD OF CHROMATOGRAPHICALLY PURIFYING OR FRACTIONATING, RESPECTIVELY, VON WILLEBRAND FACTOR FROM A VWF-CONTAINING STARTING MATERIAL

CROSS-REFERENCE TO RELATED APPLICATIONS

This application is the U.S. national phase of PCT/AT98/00020 filed Jan. 1, 1998, which claims priority from the Austrian application A 176/97 filed Feb. 4, 1997.

FIELD OF THE INVENTION

The invention relates to a method of recovering highly purified vWF or a factor VIII/vWF-complex from a biological starting material by means of collagen-affinity chromatography, as well as to a stable preparation containing highly purified vWF or factor VIII/vWF-complex.

BACKGROUND vWF is of particular importance in physiological hemostasis. Besides its function as a carrier protein for factor VIII, this plasma protein above all is necessary for the adhesion of thrombocytes to the damaged endothelium/subendothelium as well as for the aggregation of the thrombocytes under shearing stress conditions. In the first stage of primary hemostasis, the adhesion, vWF acts as a binding element between specific receptors of the thrombocyte surface, such as gpIb, gpIIb/IIIa-complex, and components of the endothelium, e.g. collagen.

According to EP 0 503 991 A, vWF is obtained in purified form from pre-purified plasma by the combination of three chromatographic purification steps. These chromatographic purification steps include a two-fold chromatography on an ion exchanger and, as a third step, an affinity chromatographic purification on gelatin sepharose. It has been shown that in gelatin sepharose chromatography, contaminating proteins, such as, e.g., fibronectin, are bound, and vWF can be obtained in the eluate.

The purification of vWF by a fractogel-EMD-TMAE chromatography with subsequent chromatography on heparin-fractogel-EMD has been described by Fischer et al. (Thromb. Res. 84 (1) (1996), 55–66).

Collagen is a physiological binding partner of vWF. Studies by Kessler et al. (Blood 63 (6) (1984), 1291–1298) have shown that the complex of vWF and factor VIII binds to collagen fibrillae, yet, however, not to denatured collagen. This result has been confirmed many times, e.g. by Santoro et al. (Collagen Rel. Res. 2 (1982), 31–43), who found out that only native collagen, yet not denatured collagen, constitutes a binding partner for vWF (cf. also Santoro, Thromb. Res. 21 (1981), 689–693, and BBA 756 (1983), 123–126; confirmed also by EP 0 503 991 A, since vWF passed the gelatine sepharose column without hindrance). It has been shown that the high molecular forms of vWF were bound by limiting low collagen concentrations. High and medium molecular forms of vWF were also bound by non-limiting high collagen concentrations, whereas the low molecular vWF fraction was not even bound at high collagen concentrations (Santoro (1983)).

This was also the reason for the fact that in assaying methods which were based on vWF collagen binding, always native collagen was used and the nativity thereof was also retained in the assay, in that denaturing conditions or strong or covalent bonds of the collagen to a solid carrier were not described in these binding assays (Brown et al., Thromb. Res. 43 (1985), 303–311).

Although the binding of collagen to vWF has been described in detail, and it has even been suggested to include this binding of vWF to native collagen in a vWF purification method (Santoro et al. (1982)), hitherto no suitable preparative method based on collagen-vWF-binding has been provided. On the one hand, this has been due to the fact that chromatographic materials based on collagen (such as, e.g., gelatine sepharose) have proven unsuitable for vWF binding, and, on the other hand, that collagen fibrillae are not suitable for the preparative recovery of vWF (cf. Santoro et al. (1982)).

SUMMARY

It is the object of the present invention to provide an improved method of purifying and recovering vWF. The method comprises absorbing vWF or factor VIII/vWF complex to immobilized collagen and recovering the adsorbed vWF or factor VIII/vWF complex by eluting the adsorbed material after removing non-adsorbed material. The method according to the preset invention results in a high proportion of physiologically active vWF and can be performed on an industrial scale.

According to the invention, this object is achieved by a method of the initially defined way which comprises the following steps:

adsorbing the vWF from the starting material on avid collagen immobilized on a carrier, separating the non-adsorbed portion and, optionally, washing the carrier, eluting the vWF from immobilized collagen, and recovering the purified vWF.

BRIEF DESCRIPTION OF THE DRAWINGS

FIG. 1 Affinity chromatography purification of vWF on Collagen agarose.

DETAILED DESCRIPTION OF THE INVENTION

By avid collagen, according to the invention collagen with a high binding capacity relative to vWF is meant. It is particularly characterized by a plurality of accessible binding sites for vWF. The criteria for selecting a suitable collagen are manifold. On the one hand, one can start from a material which is known to already have suitable binding capacities, which optionally is processed to increase its stability. Yet, processing may also be carried out to enlarge or render homogenous the surface of the immobilized collagen, which is a requirement for the reproducible extent of the adsorption of vWF. Surprisingly, the avidity of collagen could also be utilized in immobilized collagen, in contrast to the examinations of the prior art, although immobilization inevitably leads to a denaturation of the collagen molecule, particularly if immobilization is effected by covalent binding and by strong interactive forces.

Immobilization of the collagen on the solid carrier can be effected directly or indirectly, e.g. via so-called spacers. Thereby problems resulting from a steric inhibition of carrier and ligand to be immobilized are largely avoided. As the spacers, homo-or hetero-bifunctional cross-linker substances, such as hexamethylene diamine, 3,3'-diaminopropyl amine, 6-amino hexanoic acid or the hetero-bifunctional SPDP reagent from Pharmacia (Uppsala, Sweden), are, for instance, used.

In a preferred embodiment, the carrier material is previously activated by common methods, e.g. by treatment with carbodiimide or maleic acid anhydride.

Surprisingly it has been found that vWF, despite the binding of collagen to the solid carrier, enabled sufficient binding by a strong non-covalent interaction or by covalent binding. Knowing the results of Santoro et al. and also EP 0 503 991 A1, this was particularly surprising since in these investigations it was found concurring that vWF was not bound to denatured collagen.

The presence of this strong, non-covalent or covalent bond may, e.g., be confirmed by means of the assay described hereinafter: For this purpose, the collagen immobilized on a solid carrier, on which optionally also vWF is adsorbed, is treated with 0.4 mol/l NaOH for 15 minutes at room temperature. The collagen or vWF content, respectively, of the NaOH—treated material as well as of the untreated material is determined, and from the difference of the two determinations, the loss of bound collagen and, optionally, of vWF, or the reduction of the binding capacity, respectively, for vWF is determined. An immobilized collagen used according to the invention is present if the loss of collagen or of vWF, respectively, after treatment with NaOH is not more than 20%, preferably not more than 10%.

It has been shown that with the method according to the invention it not only is possible to recover vWF in a high yield, but also vWF fractions of very well defined binding activities. Accordingly, vWF preferably is recovered in more than one fraction, which fractions contain vWF with different activities, in particular with different collagen binding activities. Surprisingly it has been shown that with the method according to the invention vWF is not exclusively fractionated according to molecular weight. Commonly, however, highly active vWF fractions are those which substantially contain vWF with a high molecular portion, in particular high-molecular vWF multimers of high structural integrity.

These different fractions may, e.g., be recovered by increasing the ionic strength or the elution strength (pH, chaotropics) during the elution. Preferably, the vWF is recovered in a first fraction and at least in a second fraction, the elution of the second fraction advantageously is carried out in a solution whose ionic strength is increased by at least 20% as compared to the elution solution for the first fraction.

Elution is, e.g., carried out as a gradient elution.

Preferably, a first fraction is obtained in which vWF has a collagen binding activity of less than 0.4 U of vWF:CB/U of vWF:Ag, and a second fraction, respectively, in which vWF has a collagen binding activity of more than 0.6 U of vWF:CB/U of vWF:Ag.

It has been shown that elution of the vWF with the inventive method may be carried out with a buffer having an ionic strength corresponding to a sodium chloride concentration of at least 150 mM, in particular corresponding to an NaCl concentration in the range of from 150 mM to 400 mM.

According to a further preferred modification of the method, elution of a vWF is carried out with a buffer having an ionic strength corresponding to an NaCl concentration of less than 200 mM, in particular corresponding to an NaCl concentration in the range of from 50 mM to 150 mM, preferably in a medium having physiologic ionic strength.

According to the invention, by elution under physiological conditions, the native structure of vWF can be retained to a much greater extent, which does not only enable a more homogeneous vWF preparation but also a minimum of side reactions, e.g. by neoantigens, when administering such a vWF preparation to human.

In a further preferred embodiment, $Ca^{2+}$ ions are contained in the buffer. For instance, the content of $Ca^{2+}$ ions in the buffer is less than 10 mM, preferably less than 5 mM, so that factor VIII/vWF-complex is adsorbed on immobilized collagen. Optionally, the $Ca^{2+}$ ion content can be increased during elution from 150–200 mM so that the complex is cleaved and vWF is recovered from the complex.

The pH of the elution buffer preferably is from 5 to 9, however, also a buffer having a pH of from 3 to 4 has proven advantageous, in particular at an ionic strength of 150 mM NaCl. Moreover, the elution buffer preferably comprises chaotropic salts, in particular ammonium and/or potassium thiocyanate, a concentration of from 1 to 3 M being particularly preferred.

Since fibronectin likewise has an affinity to collagen, yet (cf. EP 0 503 991 A1) also to denatured collagen, it is possible according to the method of the invention to preparatively recover also fibronectin in a further fraction. The method according to the invention is also suitable for chromatographically purifying fibronectin.

Any solution which contains vWF is suitable as the starting material for the method according to the invention. The vWF-containing starting material in particular is human plasma, a plasma fraction or a cell culture supernatant. Preferably, however, it is started from a vWF concentrate or a commercially obtainable factor VIII/vWF-complex containing preparation.

Before carrying out the inventive adsorption step on immobilized collagen, the vWF-containing starting material advantageously is prepurified. For this, the prior art methods of ion exchange chromatography, gel permeation chromatography and/or a precipitation, preferably a precipitation with glycine or ammonium sulfate, are particularly suitable.

In a preferred embodiment, the method according to the invention is suitable as a terminal purification method. The formulation as a pharmaceutical preparation is thus simplified, since due to the physiological ionic strength (0.13–0.16 M) and the physiological osmolality (240–350, preferably 275 mOs/kg), respectively, of the medium used for elution, no further purification steps are necessary. In particular, this method also has an advantage over immuno affinity chromatography, since here, due to a possible leakage of immunoglobulin, further purification steps are necessarily required.

It has been shown that, according to the invention, a whole series of collagen types can be used, in particular collagen type I or type III (cf. e.g. Hörmann H. H ämostaseologie 1990, 10; 138–46). However, particularly the commercially available gelatine sepharose (cf. EP 0 503 991 A1) proved unsuitable for the method according to the invention, although other commercially available collagen sepharoses may very well be applied in the method of the invention, e.g. collagen agarose from Sigma.

As collagen, either collagen of human origin, or a collagen which is as far from human collagen as possible, i.e. porcine, bovine, from rat or equine, e.g.

The collagen carrier preferably is a chromatographic material to which the collagen is, e.g. covalently, bound, so that the method of the invention in particular can be used on an industrial scale.

Preferably, the collagen used according to the invention has a modification by which a stable immobilisation on the solid carrier is formed. The binding property to the protein to be purified should, of course, not be adversely affected thereby. This modification may, e.g., consist in that reactive aldehyde groups are provided in the collagen molecule.

Surprisingly, also processed collagen proved to be suitable for the present method, if the avidity of the collagen is substantially retained by such processing. The avid collagen which can be utilized according to the invention is preferably derivatized from low molecular collagen, from proteolytically processed, e.g. pepsin-digested, disintegrated or homogenized collagen. The collagen may, however, also be chemically treated or modified (derivatized); also collagen fragments may be utilized according to the invention. Advantageously, native collagen or a collagen derivative, e.g. a peptide derivatized from collagen, is utilised.

In a preferred embodiment, the vWF and/or the collagen is treated for inactivation and/or depletion of pathogens, in particular of viruses.

A number of physical, chemical or chemical/physical methods are known for the inactivation of viruses, which comprise, e.g., heat treatment, e.g. according to EP-0 159 311 A or EP-0 637 451 A, a hydrolase treatment according to EP-0 247 998 A, a radiation treatment or a treatment with organic solvents and/or tensides, e.g. according to EP-0 131 740 A. Further suitable virus inactivation steps in preparing the preparations according to the invention are described in EP-0 506 651 A or in WO-94/13329-A.

A method for inactivating or depleting viruses, respectively, may also include a filtration step, e.g. a deep filtration, ultrafiltration or nanofiltration. Besides vWF, also the collagen may accordingly be treated separately or together with the vWF, collagen may, e.g., be heat treated. If the vWF-containing starting material is, e.g., treated by adding a detergent, this detergent-containing starting material may also directly be adsorbed on the immobilized collagen. Thereby the binding capacity of the collagen for vWF can even be increased.

According to a further aspect, the present invention relates to a preparation for producing a purified vWF, which comprises biologically active vWF bound to an immobilized collagen, as well as to a pharmaceutical preparation comprising biologically active vWF which is bound to collagen in a stable manner.

A particular embodiment of the preparations according to the invention is characterized in that the vWF comprises a primary hemostatic activity, expressed by a collagen binding activity of at least 0.9 U of vWF:CB/U of vWF antigen, preferably at least 1 U of vWF:CB/U of vWF antigen, and a purity of at least 70 U of vWF antigen/mg of protein, preferably at least 80 U of vWF antigen/mg of protein.

Such vWF preparations may advantageously be prepared by the method according to the present invention, they are, however, not restricted thereto.

Advantageously, the vWF in the preparations according to the invention has a primary hemostatic activity, expressed in Ristocetin-cofactor units (U vWF:RCo) per unit of vWF:Ag of at least 0.3, preferably of at least 0.4, in particular of at least 0.6.

Furthermore, the vWF according to the preparations of the invention should possess a factor VIII binding capacity.

According to further advantageous embodiments, the preparations of the invention comprise a vWF preparation which is free from plasmatic proteins, or a vWF which is present as a factor VIII/vWF-complex, respectively.

Advantageously, the collagen in the preparations of the invention is immobilized on a solid carrier which may be selected from the group of collagen particles, synthetic carrier material, carbohydrate-based material, phospholipid and liposome. Also inorganic materials, such as, e.g., the metal hydroxide compounds common as adjuvants, can be used. The collagen particles may be globular, they may, however, also be chains, fibrillae or fibers. As solid carrier, also collagen per se may be used, if it is processed such—as already has been mentioned earlier herein—that it is suitable as a carrier.

Suitable medical possibilities of use comprise the use of the preparation according to the invention for producing a preparation for the treatment of hemophilia A as well as of diseases involving a congenital or acquired vWF deficiency. These diseases are summarized by the term vWF dysfunctions.

By providing vWF in a form bound to collagen, a physiological medicament is provided which in vivo may, e.g., imitate a vWF bound to thrombocytes. Special possibilities of use thus also comprise all those physiological functions in which the binding of vWF to thrombocyte surfaces is impaired and in which such an activity is additionally required.

Primarily if the pharmaceutical preparation is to be stored over a certain period of time, the pharmaceutical preparation is advantageously provided in lyophilized form.

Preferably, the pharmaceutical preparation is present in a form suitable for parenteral (e.g. i.v., i.m. or s.c.), mucosal (e.g. oral) or topical (e.g. as ointment) application. It is, e.g., provided as a suspension or as a solution.

The formulation of the preparation used according to the invention may be effected in a known and common manner, e.g. by aid of salts and, optionally, amino acides, yet it may also be carried out in the presence of tensides. Preferably, salts, such as, e.g., sodium chloride or calcium chloride, are used, and a pH ranging from 6 to 8 is chosen. As the amino acids, glycine or lysine are preferred. Likewise, a pharmaceutically acceptable buffer may be chosen.

The dose to be administered will particularly depend on the disease to be treated and substantially corresponds to the amounts used for factor VIII/vWF-complex or for vWF preparations, respectively.

An advantageous depot or long-term effect of the pharmaceutical preparation according to the invention is particularly provided due to the collagen present.

Suitably, the preparations according to the invention also are treated for an inactivation of pathogens possibly present, in particular viruses.

The present invention will now be explained in more detail by way of the following Examples as well as the drawing figure to which, however, it shall not be restricted.

FIG. 1 shows the chromatogram for the affinity-chromatographic purification of vWF via collagen-agarose.

EXAMPLE 1

Purification of vWF

A factor VIII/vWF-complex concentrate, prepared according to AT 391 808, comprising von Willebrand factor at a concentration of 260 U/ml vWF:Ag and a specific activity of 13.5 U vWF:Ag/mg protein was diluted with 20 mmol/l Tris buffer, pH 7.4 (=buffer A) to a vWF concentration of 6 U/ml vWF:Ag. 20 ml of this solution were applied to an affinity column (1.0×4.0 cm), filled with collagen-agarose (Sigma C-0286). After washing the column with 10 ml of buffer A, it was eluted with NaCl. For this purpose, a linear gradient of from 0 to 1 mol/l NaCl in buffer A was applied over 30 ml. Subsequently, it was washed with 10 ml of buffer B (20 mmol/l Tris, 1 mol/l NaCl, pH 7.4). The entire chromatography was carried out at a flow rate of 1 ml/min. 1 ml fractions were collected, and their optical density was determined at 280 nm. Of all the fractions, the content of vWF antigen was determined by aid of an ELISA (ASSERACHROM vWF, from Boehringer, Mannheim). The measurements showed that no vWF could be detected in the effluent in the antigen test and that a vWF antigen amount of 40 U per ml of collagen-agarose had been bound. Von Willebrand factor eluted at a NaCl concentration of 100 mmol/l. The elution diagram is illustrated in FIG. 1. After determining the protein content by aid of the Bradford assay (Anal. Biochem. 72, 248–254, 1976), there resulted a purity of vWF of 85 U vWF:Ag/mg protein in the elution maximum. For the activity of vWF values of 0.47 U vWF:RCo/U vWF:Ag as well as 0.45 U vWF:CB/U vWF:Ag were determined.

EXAMPLE 2

Fractionation of vWF

A highly purified vWF concentrate according to EP 0 567 448 comprising von Willebrand factor at a concentration of 105 U/ml vWF:Ag and a specific activity of 60 U vWF:Ag/mg protein was diluted with 20 mmol/l Tris buffer, pH 7.4 (=buffer A) to a vWF concentration of 4 U/ml of vWF:Ag. 20 ml of this solution were applied to an affinity column (1.0×4.0 cm) filled with collagen-agarose (Sigma 0–0286). After washing the column with 10 ml of buffer A, it was eluted with an NaCl stage gradient. For this purpose, the column was eluted with 10 ml each of buffer B (0.15 mol/l NaCl in buffer A), buffer C (0.3 mol/l NaCl in buffer A), buffer D (0.5 mol/l NaCl in buffer A) and buffer E (1 mol/l NaCl in buffer A). Buffer E served to regenerate the column. The entire chromatography was carried out at a flow rate of 1 ml/min. 1 ml fractions were collected and their optical density was determined at 280 nm. The vWF antigen content of all these fractions was determined by aid of an ELISA (ASSERACHROM vWF, from Boehringer, Mannheim). The measurements showed that an antigen amount of 23 U per ml of collagen-agarose was bound and that an antigen amount of a total of 3 U eluted in the effluent. Von Willebrand factor eluted from the column with buffers B, C and D and had a purity of 75 U vWF:Ag/mg protein. In the various eluates, the following activities were determined:

| U vWF:RCo/U vWF:Ag | Activity U vWF:CB/U vWF:Ag |
|---|---|
| Eluate buffer B: 0.41 | 0.46 |
| Eluate buffer C: 0.68 | 0.70 |
| Eluate buffer D: 0.91 | 0.87 |

EXAMPLE 3

Purification of Factor VIII/vWF-Complex

To isolate a factor VIII/vWF-complex, a cryoprecipitate, prepared according to Pool et al. (N.Engl.J.Med. 273, 1443–1447, 1965) was dissolved in 20 mmol/l Tris buffer, pH 7.4. 20 ml of a solution containing 6 U vWF:Ag/ml and 5.5 U/ml factor VIII:c (IMMUNOCHROM F VIII:c-Test, from Immuno) were applied to a column filled with collagen-agarose. Affinity chromatography was carried out analogous to Example 1. The content of von Willebrand factor antigen as well as of factor VIII:c was determined of each fraction. Von Willebrand factor was eluted from the column in complex together with factor VIII:c at an NaCl concentration of 100 mmol/l.

EXAMPLE 4

Preparation of a Highly Purified vWF Concentrate

To prepare a highly purified von Willebrand factor concentrate for pharmaceutical use, an affinity chromatographic purification was carried out according to Example 1. Application of the samples onto the affinity column was in 20 mmol/l sodium citrate buffer, pH 7.3. The fractions having a specific activity of more than 70 U vWF:Ag/mg protein were collected, stabilized by the addition of 5 g of glycine and 5 g of L-lysine per liter, a pH of 7.0 was adjusted with 0.1 mol/l NaOH, and subsequently they were freezed-dried. Upon reconstitution with $H_2O$, an osmolality (Pharmak. Europ., 2nd Ed. V.6.25) of 350 mOsmol/kg $H_2O$ was determined for this preparation.

EXAMPLE 5

Immobilisation of Collagen (at present by applicant considered the best mode of carrying out the invention)

To prepare an affinity resin with covalently immobilized collagen, 25 mg of acid-soluble type III collagen from human placenta (Sigma C-4407) were dissolved in 10 ml 0.1 M acetic acid at 40° C. and shaken with care for 6 h at this temperature. Subsequently, it was filtered through a filter having a pore diameter of 0.4 μm, the filtrate was added to a suspension of 5 ml ECH-Sepharose® 4B (Pharmacia), and a pH of 4.5 was adjusted by the addition of 0.1 mol/l NaOH. Over a period of 2 hours, a total of 300 mg of 1-ethyl-3-(3-dimethylaminopropyl)-carbodiimide hydrochloride (EDC/from Pierce) were added at a temperature of 40° C., in 30 mg portions under constant stirring by using a stirrer operated by an electric motor. Subsequently, stirring was continued for further 6 hours at 40° C. During the entire reaction time, the pH was checked by aid of a pH electrode and maintained in a range of from 4.5 to 5.0 by adding 0.1 mol/l NaOH. The affinity gel thus prepared was washed first with 20 ml of sodium acetate buffer (0.1 mol/l acetate, 0.5 mol/l NaCl, pH 4.3), as well as with 20 ml of Tris buffer (0.1 mol/l Tris, 0.5 mol/l NaCl, pH 7.8) at room temperature, and this process was repeated twice. After washing the gel with $H_2O$ as well as with the buffer system used for binding vWF in the subsequent affinity chromatography, the gel was used as described in Examples 1 to 4 for purifying vWF.

EXAMPLE 6

Purification of vWF With Modified Collagen a) Dissolution of Collagen

Human collagen, type III, was dissolved at 5 mg/ml in 500 mM acetic acid at 4° C., and subsequently diluted with water to 1 mg/ml. The dissolved collagen was stored at −20° C.

b) Chemical Modification of Collagen

For a chemical modification, the collagen of Example 6 a) was diluted in 10 mM Na acetate buffer, pH 4, to 10 μg/ml. To 10 ml of this solution, 32 mg $NaIO_4$ were added, and the reaction was carried out for 0.5 h at room temperature. This reaction results in a chemical modification, with reactive aldehyde groups forming in the collagen molecule.

c) Chemical Coupling of Modified Collagen to a Solid Carrier

Human collagen was activated according to Example 6 b) with Na periodate. Activated collagen was covalently coupled to an amino group-containing carrier, adipin hydrazide sepharose (from Pharmacia), via the activated carbohydrate portion of the collagen and the amino group of the carrier.

d) Purification of vWF From a vWF-containing Solution

To purify vWF, 10 ml of a vWF-containing solution having an initial activity of vWF of 900 mU/ml vWF:RistoCoF were contacted with the carrier consisting of collagen adipinic acid hydrazide sepharose, and the vWF was bound to the carrier. Non-bound proteins were washed off the carrier by washing with a buffer containing 50 mM Tris/HCl, pH 7.4, 150 mM NaCl. Bound vWF was eluted from the carrier with a buffer containing 50 mM Tris/HCl, pH 7.4, 150 mM NaCl, 1.5 M KSCN. The eluate was tested for vWF activity. The vWF activity in the eluate was 1500 mU/ml vWF:RistoCoF. Gel electrophoretic analysis shows that the eluate contains particularly high molecular vWF multimers.

What is claimed is:

1. A method of chromatographically purifying von Willebrand factor (vWF) derived from a vWF-containing starting material, said method comprising
   (a) adsorbing vWF contained in said starting material on avid collagen, said avid collagen being immobilized on a carrier and in denatured form,
   (b) separating a non-absorbed portion of said starting material,
   (c) eluting vWF from said immobilized collagen, thereby recovering a purified vWF.

2. A method as set forth in claim 1, further comprising washing said carrier after said separating of said non-adsorbed portion of said starting material.

3. A method as set forth in claim 1, wherein eluting to provide purified vWF is effected by fractionated elution.

4. A method as set forth in claim 3, wherein said vWF is recovered in more than one fraction.

5. A method as set forth in claim 4, wherein said vWF is recovered in a first fraction and in at least a second fraction, elution of said second fraction being effected with a solution having an ionic strength higher by at least 20% as compared to an elution solution used for said first fraction.

6. A method as set forth in claim 4, wherein said eluting is carried out as a gradient elution.

7. A method as set forth in claim 4, wherein a first fraction is obtained in which vWF has a collagen binding activity of less than 0.4 U vWF:CB/U vWF:Ag, and a second fraction is obtained in which vWF has a collagen binding activity of more than 0.6 U vWF:CB/U vWF:Ag.

8. A method as set forth in claim 4, wherein eluting is effected in a first and a second fraction, eluting of said second fraction being effected with a buffer having an ionic strength corresponding to an NaCl concentration of at least 150 mmol/l.

9. A method as set forth in claim 8, wherein said buffer has an ionic strength corresponding to an NaCl concentration ranging from 150 to 400 mmol/l.

10. A method as set forth in claim 1, wherein eluting is effected in a first and at least one second fraction, eluting of said first fraction being effected with a buffer having an ionic strength corresponding to an NaCl concentration of less than 200 mmol/l.

11. A method as set forth in claim 10, wherein said buffer has an ionic strength corresponding to an NaCl concentration ranging from 50 to 150 mmol/l.

12. A method as set forth in claim 10, wherein said eluting is carried out in a medium having physiological ionic strength.

13. A method as set forth in claim 3, further comprising recovering fibronectin in a further fraction.

14. A method as set forth in claim 1, wherein said vWF-containing starting material is selected from the group consisting of a vWF concentrate and a preparation containing a complex between factor VIII and vWF.

15. A method as set forth in claim 1, further comprising pre-purifying said vWF-containing starting material before said adsorbing of said vWF contained in said starting material on said avid collagen immobilized on said carrier.

16. A method as set forth in claim 15, wherein said pre-purifying is effected by at least one pre-purification method selected from the group consisting of ion exchange chromatography, gel permeation chromatography and precipitation.

17. A method as set forth in claim 16, wherein said pre-purifying is a precipitation carried out with an agent selected from the group consisting of glycine and ammonium sulfate.

18. A method as set forth in claim 1, wherein said purified vWF is recovered in a medium having physiological ionic strength, further comprising processing said purified vWF to a pharmaceutical preparation without any further purification steps.

19. A method as set forth in claim 1, wherein said purified vWF is recovered in a medium having physiological osmolality, further comprising processing said purified vWF to a pharmaceutical preparation without any further purification steps.

20. A method as set forth in claim 1, wherein said collagen is selected from the group consisting of collagen type I and collagen type III.

21. A method as set forth in claim 1, wherein said collagen is a collagen selected from the group consisting of human, porcine, bovine, rat and equine origin.

22. A method as set forth in claim 1, wherein said collagen comprises at least one modification by which a stable immobilization on said solid carrier is formed.

23. A method as set forth in claim 22, wherein said modification in said collagen is a formation of reactive aldehyde groups.

24. A method as set forth in claim 1, wherein said carrier is a chromatographic carrier to which said collagen is bound.

25. A method as set forth in claim 24, wherein said collagen is covalently bound to said chromatographic carrier.

26. A method as set forth in claim 1, wherein said carrier comprises processed collagen.

27. A method as set forth in claim 1, further comprising subjecting at least one of said vWF and said collagen to a treatment, wherein said treatment is selected from the group consisting of a pathogen inactivation treatment, a pathogen depletion treatment, and combinations thereof.

28. A method as set forth in claim 27, wherein said pathogens are viruses.

29. A method as set forth in claim 22, wherein eluting of said vWF is effected with a buffer having a pH ranging from 5 to 9.

30. A method as set forth in claim 29, wherein said buffer for said eluting of said vWF has a pH ranging from 3 to 4.

31. A method as set forth in claim 22, wherein said eluting of said vWF is effected with a buffer comprising a chaotropic salt.

32. A method as set forth in claim 31, wherein said chaotropic salt is at least one of ammonium thiocyanate and potassium thiocyanate.

33. A method as set forth in claim 31, wherein said chaotropic salt has a concentration of from 1 to 3 M.

34. A preparation for producing a purified vWF comprising a biologically active vWF and an immobilized denatured collagen, said biologically active vWF being bound to said immobilized denatured collagen.

35. A preparation as set forth in claim 34, wherein said vWF has a primary hemostatic activity expressed by a collagen binding activity of at least 0.9 U vWF:CB/U vWF:Ag and has a purity of at least 70 U vWF:Ag/mg protein.

36. A preparation as set forth in claim 35, wherein said collagen binding activity is at least 1 U vWF:CB/U vWF:Ag.

37. A preparation as set forth in claim 35, wherein said purity is at least 80 U vWF:Ag/mg protein.

38. A preparation os set forth in claim 34, wherein said vWF has a primary hemostatic activity expressed in U vWF:CB/U vWF:Ag of at least 0.3.

39. A preparation as set forth in claim 38, wherein said primary hemostatic activity is at least 0.4.

40. A preparation as set forth in claim 38, wherein said primary hemostatic activity is at least 0.6.

41. A preparation as set forth in claim 34, wherein said vWF is present as a factor VIII/vWF-complex.

42. A preparation as set forth in claim 34, wherein said vWF is free from plasmatic proteins.

43. A preparation as set forth in claim 41, wherein said factor VIII/vWF-complex is free from plasmatic proteins.

44. A preparation as set forth in claim 34, wherein said collagen is immobilized on a solid carrier selected from the group consisting of collagen particles, synthetic carrier material, carbohydrate-based material, phospholipid and liposome.

45. A preparation as set forth in claim 34, wherein said collagen is selected from the group consisting of native collagen, a collagen derivative, an enzymatically processed collagen and a collagen fragment.

46. A preparation as set forth in claim 34, said preparation being present in lyophilized form.

47. A preparation as set forth in claim 34, said preparation having been treated by a treatment, wherein said treatment is selected from a group consisting of a pathogen inactivation treatment, a pathogen depletion treatment, and combinations thereof.

* * * * *

UNITED STATES PATENT AND TRADEMARK OFFICE
CERTIFICATE OF CORRECTION

PATENT NO. : 6,414,125 B1 Page 1 of 1
DATED : July 2, 2002
INVENTOR(S) : Juergen Siekmann, Peter Turecek, Hans-Peter Schwarz, Johann Eibl, Bernhard Fischer Artur Mitter and Friedrich Dorner It is certified that error appears in the above-identified patent and that said Letters Patent is hereby corrected as shown below:

Drawings,
Figure 1, Title of Fig. 1 should read -- Affinity chromatographic purification of vWF via collagen agarose --
Title of the y-axis on the right side should read -- U/ml --.
Title of the x-axis should read -- Fraction number --.
Last line of legend should read -- vWF:Ag (U/ml) --.

Column 2,
Line 18, the "absorbing" should read -- adsorbing --.
Line 22, the "preset" should read -- present --.

Column 4,
Lines 51-52 the "H ämostaseologie" shoudld read -- Hämostaseologie --.

Column 8,
Lines 31, 38 and 41 the "40º C." should read -- 4º C. --.

Column 9,
Lines 26-27, the "(b) separating a non-absorbed portion of said starting material," should read -- (b) separating a non-adsorbed portion of said starting material, --.

Signed and Sealed this

Twenty-sixth Day of November, 2002

*Attest:*

JAMES E. ROGAN
*Attesting Officer* *Director of the United States Patent and Trademark Office*